(12) United States Patent
Voznesensky et al.

(10) Patent No.: US 8,755,888 B2
(45) Date of Patent: Jun. 17, 2014

(54) GASTROINTESTINAL SYSTEM (71) Applicants: Boris Voznesensky, Netanya (IL); Josef More, Herzliya (IL)

(72) Inventors: Boris Voznesensky, Netanya (IL); Josef More, Herzliya (IL)

(73) Assignee: Melcap Systems Ltd., Ramat Gan (IL)

( * ) Notice: Subject to any disclaimer, the term of this patent is extended or adjusted under 35 U.S.C. 154(b) by 0 days.

(21) Appl. No.: 13/799,205

(22) Filed: Mar. 13, 2013

(65) Prior Publication Data

US 2014/0107726 A1    Apr. 17, 2014

Related U.S. Application Data (60) Provisional application No. 61/714,756, filed on Oct. 17, 2012.

(51) Int. Cl.
*A61N 1/00* (2006.01)

(52) U.S. Cl.
USPC .......................................................... 607/40

(58) Field of Classification Search
USPC .......................................................... 607/40
See application file for complete search history.

(56) References Cited

U.S. PATENT DOCUMENTS

| | | |
|---|---|---|
| 5,423,872 A | 6/1995 | Cigaina |
| 5,690,691 A | 11/1997 | Chen et al. |
| 6,098,629 A | 8/2000 | Johnson et al. |
| 6,285,897 B1 | 9/2001 | Kilcoyne et al. |
| 6,453,199 B1 | 9/2002 | Kobozev |
| 6,571,127 B1 | 5/2003 | Ben-Haim et al. |
| 6,689,056 B1 | 2/2004 | Kilcoyne et al. |
| 6,889,076 B2 | 5/2005 | Cigaina |
| 7,076,305 B2 | 7/2006 | Imran et al. |
| 7,107,100 B2 | 9/2006 | Imran et al. |
| 7,221,978 B2 | 5/2007 | Ben-Haim et al. |
| 7,738,961 B2 | 6/2010 | Sharma |
| 7,840,269 B2 | 11/2010 | Policker |
| 8,160,709 B2 | 4/2012 | Soffer et al. |
| 2003/0114895 A1 | 6/2003 | Gordon et al. |
| 2010/0121420 A1* | 5/2010 | Fiset et al. ...................... 607/94 |
| 2010/0305655 A1* | 12/2010 | Raffle et al. ..................... 607/40 |

* cited by examiner

*Primary Examiner* — George Manuel
(74) *Attorney, Agent, or Firm* — JMB Davis Ben-David (57) ABSTRACT

A gastrointestinal stimulation system includes a remote controlled capsule adapted for positioning in the gastrointestinal tract (GT) of a patient, in which the capsule is secured to the inner wall of the gastrointestinal tract (GT) of a patient by a magnetic coupling system. The capsule is configured to activate at least one chosen area of the patient's GI tract, including when desired, the vagus nerve, thereby facilitating gastro motility or having other interaction with the GI tract, such as monitoring thereof. The remote controlled capsule also may be configured to activate patient's lower esophageal sphincter (LES), stimulating the LES muscle and restoring the barrier between the stomach and the esophagus for treatment of Gastroesophageal reflux disease (GERD). The capsule also may be inserted to the anal canal for treatment of constipation.

11 Claims, 10 Drawing Sheets

GASTROINTESTINAL SYSTEM

CROSS REFERENCE TO RELATED APPLICATION

This application claims priority to U.S. Provisional Patent Application No. 61/714,756, filed on Oct. 17, 2012.

FIELD OF THE INVENTION

The present invention relates to systems for treating gastrointestinal disorders.

BACKGROUND OF THE INVENTION

There are known in the art various devices for the electrical stimulation of the vagus nerve or other portions of gastrointestinal tract (GT), in order to provide relief or treatment of gastrointestinal disorders. Such devices are also known for the treatment of obesity.

The known art includes US patent application publication no. 2003/0114895 A1 and U.S. Pat. Nos. 5,423,872, 5,690, 691, 6,098,629, 6,285,897, 6,453,199, 6,571,127, 6,689,056, 6,889,076, 7,076,305, 7,107,100, 7,221,978, 7,738,961, 7,840,269 and 8,160,709.

SUMMARY OF THE INVENTION

The present invention provides a gastrointestinal stimulation system including a remote controlled capsule adapted for positioning in the gastrointestinal tract (GT) of a patient, in which the capsule is secured to the inner wall of the gastrointestinal tract (GT) of a patient by a magnetic coupling system. The capsule is configured to activate at least one chosen area of the patient's GI tract, including when desired, the vagus nerve, thereby facilitating gastro motility or having other interaction with the GI tract, such as monitoring thereof. The remote controlled capsule also may be configured to activate patient's lower esophageal sphincter (LES), stimulating the LES muscle and restoring the barrier between the stomach and the esophagus for treatment of Gastroesophageal reflux disease (GERD). The capsule also may be inserted to the anal canal for treatment of constipation.

There is thus provided in accordance with an embodiment of the invention, a gastrointestinal electro stimulation system including:

(I) a remote controlled capsule adapted for ingression into the gastrointestinal tract of a patient, (II) a remote control device for controlling and sharing information with the capsule, and (III) a magnetic coupling system for securing the capsule within the gastrointestinal tract of the patient, wherein the capsule has a main body main body portion and a plurality of electrodes arranged in electrical isolation from each other, the capsule containing:

(a) a first RF transceiver operative to receive capsule operating instructions from and to transmit information to the remote control device;

(b) a capsule control unit electrically coupled to the first RF transceiver and operative to process the received operating instructions;

(c) a pulse generator electrically coupled to the capsule control unit and to the electrodes and configured to activate the electrodes so as to emit electrical stimuli pulses in accordance with the operating instructions; and (d) a power supply for supplying electrical power to the first RF transceiver, to the control unit and to the pulse generator, wherein the remote control device includes:

(e) a system control unit operative to generate the operating instructions;

(f) a second RF transceiver coupled to the system control unit and configured to transmit the operating instructions and to receive information from the first RF transceiver, and wherein the magnetic coupling system includes:

(g) a first magnetic element associated with the capsule and a second magnetic element configured for placement externally of the body of patient, wherein selectable operation of the pulse generator is operative to expose to electrical stimuli a portion of the gastrointestinal tract where the capsule is secured.

Additionally in accordance with an embodiment of the invention, the first magnetic element includes a permanent magnet arranged within the capsule.

Further in accordance with an embodiment of the invention, the system also includes position sensor apparatus for sensing the position of the capsule.

Additionally in accordance with an embodiment of the invention, the position sensor unit includes a magnetic field sensor.

Further in accordance with an embodiment of the invention, the position sensor apparatus includes:

a capsule position verification system having two or more electrodes located externally of the patient;

a recording module connected to the two or more externally located electrodes, and having an output adapted to provide capsule position output data to the system control unit of remote control device.

Additionally in accordance with an embodiment of the invention, the capsule and the contents thereof have a specific weight approximately equal to the specific weight of stomach juices.

Further in accordance with an embodiment of the invention, wherein the capsule also contains one or more sensors of a predetermined type coupled to the capsule control unit, wherein the one or more sensors is selected from the group which consists of:

a pH-sensor,
a pressure sensor,
an electric impedance sensor,
a temperature sensor, and
an electrical muscular activity sensor.

Additionally in accordance with an embodiment of the invention, the capsule is further adapted for egression from the pyloric region of the gastrointestinal tract after at least a predetermined dwell time therein, and wherein main body portion of the capsule includes:

one or more gastric juice-responsive expandable elements adapted for storage within a storage compartment formed within the main body portion of the capsule; and a gastric-juice responsive cover for the storage compartment which when closed, prevents the one or more expandable elements from exposure to gastric juices and, when open, facilitates exposure of the one or more expandable elements to gastric juices such that the element expands so as to be forced out of the storage compartment and so as to increase the overall size of the capsule system thereby preventing the system from egression from the pyloric region of the stomach;

wherein the one or more expandable elements are connected to the main body portion of the capsule by means of a gastric-juice responsive releasable connector element.

Further in accordance with an embodiment of the invention, the gastric-juice responsive cover is formed of a first gastric-juice soluble substance which is soluble at a first predetermined rate so as to permit exposure of the expandable element to gastric juices after a first dwell time in the gastrointestinal tract of a patient, and the gastric-juice responsive releasable connector element is formed of a second gastric-juice soluble substance which is soluble at a second predetermined rate so as to dissolve the connector element after a second dwell time in the gastrointestinal tract of a patient, the second dwell time being longer than the first dwell time, wherein dissolution of the connector element causes detachment of the one or more expandable elements from the main body portion of the capsule, thereby permitting egression of the capsule from the gastrointestinal tract.

Additionally in accordance with an embodiment of the invention, each the expandable element is adapted to expand to a size which is sufficiently small to permit egression thereof from the gastrointestinal tract.

In accordance with a further embodiment of the invention, there is provided an extendible capsule adapted for ingression into the gastrointestinal tract of a patient, which includes:
  first and second capsule portions;
  a resilient element disposed between the first and second capsule portions for normally urging them apart into an extended arrangement; and
  a gastric juice-responsive release unit operative to retain the first and second capsule portions in a non-extended arrangement in a first operative state of the capsule, and further operative, in response to contact with gastric juices for at least a predetermined period of time to permit the capsule to move into a second operative state by mutual extension of the first and second capsule portions thereby to extend the effective length of the capsule.

Additionally in accordance with an embodiment of the invention, the gastric juice-responsive release unit includes:
  a first gastric juice-responsive locking element for resisting an urging force of the resilient element, thereby locking together the first and second capsule portions in the non-extended arrangement when the capsule is in the first operative state; and
  a second gastric juice-responsive, selectably releasable locking element operative to maintain a mechanical connection between the first and second capsule portions when the capsule is in the extended arrangement in the second operative state, wherein the first and second locking elements are adapted to selectably disconnect the first and second capsule portions from each other so as to move the capsule into a third operative state,
  wherein, when the capsule is in the first operative state, the first locking element is deactivated, such that the resilient element is operative to force the first and second capsule portions and thus the capsule into the extended arrangement of the second operative state,
  and wherein, the second locking element is subsequently deactivated so as to disconnect the first and second capsule portions from each other such that the capsule splits into two portions and moves into the third operative state.

Further in accordance with an embodiment of the invention, the gastric juice-responsive release unit is formed of a solid substance which is soluble in gastric juices.

Additionally in accordance with an embodiment of the invention, the first gastric juice-responsive locking element is formed of a first gastric-juice soluble substance which is soluble at a first predetermined rate so as to permit extension of the capsule after a first dwell time in the gastrointestinal tract of a patient, and the second gastric juice-responsive locking element is formed of a second gastric-juice soluble substance which is soluble at a second predetermined rate so as to disconnect the first and second capsule portions from each other permit after a second dwell time in the gastrointestinal tract of a patient, the second dwell time being longer than the first dwell time.

Further in accordance with an embodiment of the invention, the first capsule portion includes a main body portion formed of a dielectric material, and a first electrode, and the second capsule portion includes a second electrode,
  wherein the first capsule portion contains:
    (i) an RF transceiver operative to receive capsule operating instructions from a remote control unit and to transmit information thereto;
    (ii) a capsule control unit electrically coupled to the RF transceiver and configured to process received operating instructions;
    (iii) a pulse generator electrically coupled to the capsule control unit and to the first and second electrodes and configured to activate the first and second electrodes so as to emit electrical stimuli pulses in accordance with the processed operating instructions, and
    (iv) a power supply for supplying electrical power to the RF transceiver, to the control unit and to the pulse generator,
  and wherein upon extension of the capsule, the first and second electrodes are moved laterally apart so to increase the distance between them, and thus to expose a greater portion of the GI tract to the electrical stimuli pulses.

There is also provided, in accordance with yet a further embodiment of the invention, for use with a gastrointestinal capsule system which includes a capsule adapted for ingression into the gastrointestinal tract of a patient, and a magnetic coupling system for securing the capsule within the gastrointestinal tract of the patient, wherein the coupling system has a first magnetic element associated with the capsule and a second magnetic element configured for placement externally of the body of the patient,
  one or more capsule-securing devices implantable in the wall of the gastrointestinal tract at selected locations, the capsule-securing device including:
    a location pin; and
    a third magnetic element associated with the location pin,
    wherein, when the capsule is located within the gastrointestinal tract of the patient, movement of the second magnetic element, externally of the patient's body, to a position corresponding to that of the capsule-securing device, causes a corresponding movement of the first magnetic element and a consequent magnetic coupling of the first and the third magnetic elements, thereby to position the capsule at the selected location in the gastrointestinal tract.

Additionally in accordance with an embodiment of the invention, the location pin includes:
  a pin head having an upper surface to which the third magnetic element is secured and a lower surface for engaging the wall of the gastrointestinal tract when implanted therein; and
  a pin shaft extending from the lower surface and having a serrated outer edge for mechanically securing the device to the inner wall of the gastrointestinal tract.

Further in accordance with an embodiment of the invention, the system is a gastrointestinal system and the capsule is used for gastrointestinal electro stimulation, and wherein the capsule-securing device is formed of an electro-conductive material.

BRIEF DESCRIPTION OF THE DRAWINGS

The invention is herein described, by way of example only, with reference to the accompanying drawings, in which like components are designated by like reference numerals, wherein.

DETAILED DESCRIPTION

Figure 1A:
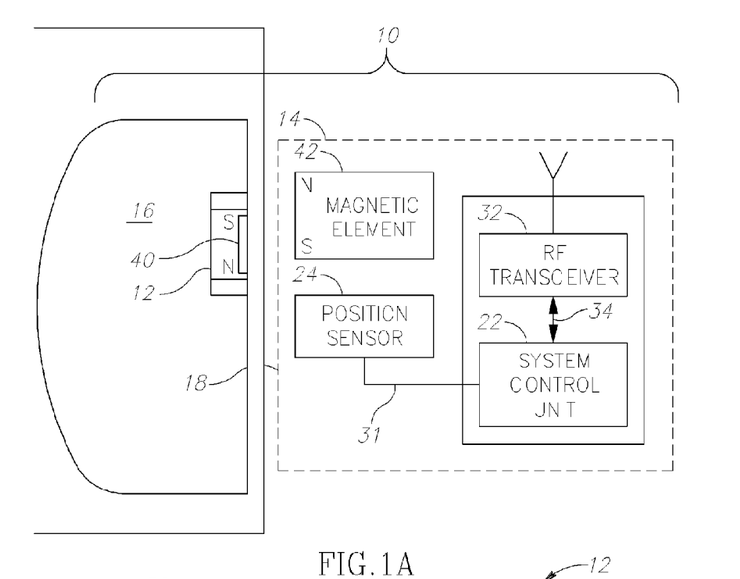
FIG. 1A is a schematic representation of a gastrointestinal (GT) stimulation system, constructed and operative in accordance with a preferred embodiment of the present invention.

Reference is now made to FIG. 1A, which is a schematic representation of a gastrointestinal stimulation system 10, constructed and operative in accordance with an embodiment of the present invention. System 10 includes, inter alia, a remotely controlled capsule 12 and a control device 14 for controlling and monitoring the operation of capsule 12. In use, capsule 12 is swallowed by a patient. After it has entered the gastrointestinal tract (GT) 16 of the patient it is secured to the inner wall 18 of the GT 16 by means of a magnetic coupling system, as described below. Capsule 12 may have an external enteric coating, which remains stable in the relatively less acidic juices (pH≈3) of the stomach, but dissolves in the alkaline juices (pH≈7-9) in the small intestine. Materials used for enteric coated may be, inter alia, fatty acids, waxes, Shellac, plastics, and plant fibers.

Control device 14 includes, inter alia, a system control unit 22 and a position sensor 24. System control unit 22 is configured to receive input instructions and parameters from an operator and/or medical personnel in accordance with medical requirements of the patient, to provide capsule operating instructions and parameters to capsule 12 and to otherwise share information therewith.

Position sensor 24 senses, inter alia, the position of capsule 12, as described below and is configured to locate capsule 12 at the required location in the GT 16, in accordance with instructions received from the system control unit 22. The system control unit 22 and the position sensor 24 intercommunicate via a communications link 31.

There is also provided an RF transceiver 32 which communicates with system control unit 22 via a communications bus 34. Capsule operation instructions and other data are transmitted to capsule 12 via a wireless communications link (not shown in FIG. 1A).

The parameters and information forwarded by the system control unit 22 to capsule 12 and received therefrom may also be forwarded to a user-notification device with a user interface (not shown). Thus, the operation of the stimulation system 10 may be monitored and controlled by the operator and/or user.

The RF transceiver 32 also receives feedback information from capsule 12, such as the location of capsule 12, as described below. The RF transceiver 32 forwards the information to the system control unit 22, which then forwards this information to the user-notification device for notifying the operator of the location of capsule 12, as described below.

The required instructions and parameters for the operation of the stimulation system 10 are inputted via a suitable data input device associated with the control unit 22. The data input device (not shown) may be a radio frequency (RF) operated remote control unit, an RF transmitter, an RF transceiver, a cellular telephone, a 3G cellular telephone, a smartphone, an ultrasonic transmitter, an ultrasonic transceiver, an infrared (IR) transmitter, an infrared transceiver, a Bluetooth® communication device, an iPod®, an iPAD®, an android tablet, a laptop computer, any suitable device with wireless communication capability and any combinations thereof. Various portions of the system control system may be implemented as one or more Smartphone software application.

In alternative embodiments of the invention, RF transceiver 32 can be replaced by an ultrasonic transceiver for transmitting the capsule operating instructions to capsule 12 and for receiving feedback information from capsule 12. In such an embodiment, capsule 12 may include a microphone or any type of acoustic sensor which is suitably linked to the control unit 22 and is operational to activate, deactivate and/or control the operation of capsule 12.

The above-mentioned magnetic coupling system for coupling capsule 12 to control device 14 includes first and second magnetic elements, respectively referenced 40 and 42. First magnetic element 40 is associated with capsule 12 and second magnetic element 42 is associated with control device 14 and is located externally to the patient's body. The position sensor 24 includes, inter alia, a magnetic field position sensor such as Hall Effect Sensor, which senses the position of capsule 12 within the GT 16, by measuring the output voltage in response to a magnetic field. Preferably, first magnetic element 40 is located in main body portion 50 of capsule 12, as described below in conjunction with FIG. 1B.

Magnetic elements 40 and 42 may be formed of any of a variety of materials, such as a suitable ferromagnetic material, a ceramic composite, a ferrite composite, an injection molded magnet, a magnet constructed from a flexible material, such as FlexIRON™ and a rare-earth magnet, such as a Neodymium magnet. Additionally or alternatively, the magnetic element 42 is an electromagnet.

Figure 1B:
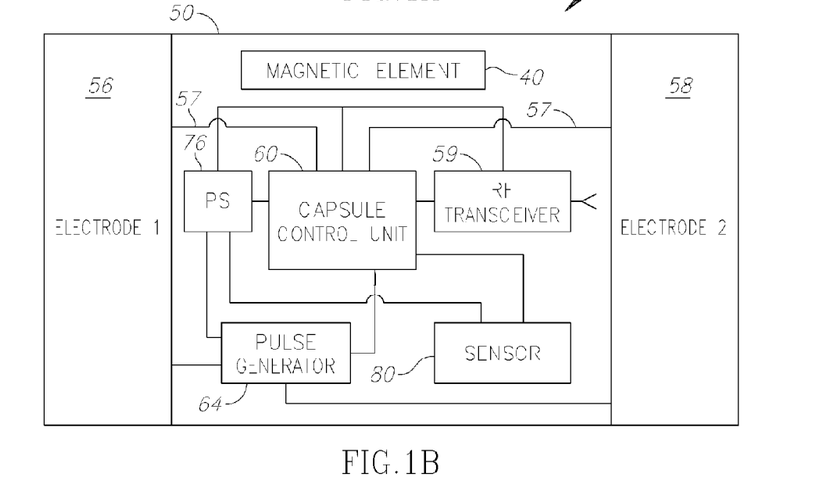
FIG. 1B is a schematic representation of the capsule depicted in FIG. 1A, in accordance with a preferred embodiment of the present invention.

Reference is now made to FIG. 1B, which is a schematic layout of capsule 12, in accordance with an embodiment of the present invention. Capsule 12 has a main body portion 50 and at least first and second electrodes, respectively referenced 56 and 58. It will be appreciated that there may be advantageously provided additional electrodes and that they are electrically isolated from each other. Typically, this is provided by forming the main body portion 50 of a dielectric material. Further, main body portion 50 and first and second electrodes 56 and 58 are sealed together in a suitable manner, which may be mechanical, bonding, welding and the like. Capsule 12 includes, inter alia, an RF transceiver 59 for transmitting capsule status information as well as for receiving capsule operating instructions and parameters from the remote control device 14 via the above-described communications link. Capsule 12 also includes a capsule control unit 60, which is electrically coupled to the RF transceiver 59.

It will be appreciated that electrodes 56 and 58 may be located on one side of capsule 12 only, and in this case, while dielectric main body portion 50 as it shown on FIG. 1B is not located in the center of the capsule.

Capsule control unit 60 receives data, such as the capsule operating instructions and parameters via RF transceiver 59, and also provides data, such as capsule location information, to RF transceiver 59, as shown.

The capsule control unit 60 includes a processor for processing instructions and parameters received via RF transceiver 59. Unit 60 forwards to a pulse generator 64 instructions for the pulse generator 64 to generate pulses with specific parameters which conform to medical instructions inputted into the system 10 as described above.

Pulse generator 64 is operative to generate electrical stimuli pulses in accordance with the received instructions and parameters, and taking into consideration additional factors such as tissue impedance, forwarding pulses to the first and second electrodes 56 and 58. The operating instructions conveyed from control device 14 to capsule 12 include the technical specifications of the stimuli pulses to be generated by the pulse generator 64. These include the amplitude, frequency, and waveform and duty cycle of the pulses.

It is appreciated that the technical specifications of the stimulation signals are dependent on the gastro disorder to be treated, as described below.

Capsule 12 further includes a sensor unit 80 for sensing GT parameters and forwarding them to control unit 60. Sensor unit may include one or more of a fluid pressure sensor, a fluid pressure gradient sensor, a temperature sensor, a pH-sensor, a bio-potential sensor, an acoustical sensor, a mechanical sensor (strain gauge for instance), an electrical conductivity sensor, an electric impedance sensor, a sensor for measuring muscle activity or any combination thereof. Control unit 60 forwards the received data to the RF transceiver 59, which transmits the data to the control device 14 for analysis and interpretation by the operator. Sensor unit 80 thus enables the operator both to determine the location of capsule 12 and to monitor its operation.

A power supply 76, which may be a direct current power source, an alternating current power source, a battery, a primary electrochemical cell, a rechargeable electrochemical cell, a mechanical power source, or any combination thereof, supplies electrical operational power to RF transceiver 59, control unit 60, pulse generator 64 and sensor unit 80.

In addition, capsule 12 and all elements included therewithin as described above, preferably have a specific weight approximately equal to the specific weight of gastric juices. This enables capsule 12 to float thereon, thereby in turn enabling a user to relatively easily control the movement of capsule 12 by means of second magnetic element 42.

Figure 2:
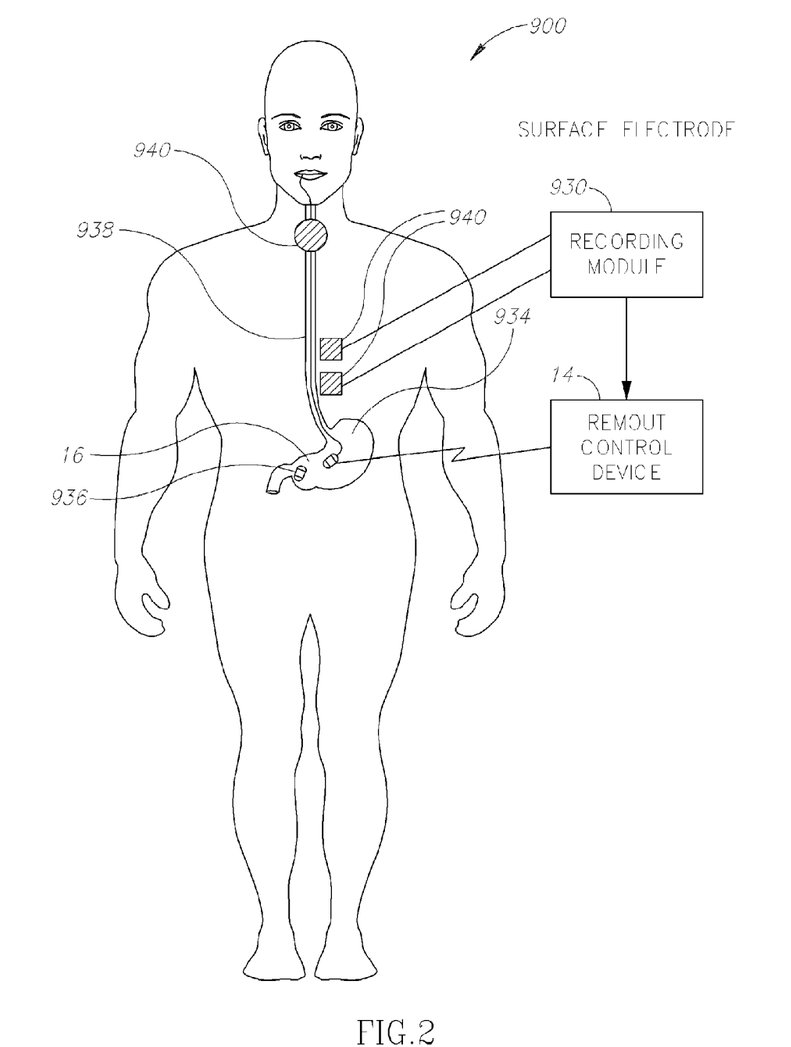
FIG. 2 shows a Nerve Conduction Study system electrically coupled to at least one branch of the vagus nerve or other chosen region of the GT of a patient for sensing the location of the capsule relative thereto, in accordance with an embodiment of the present invention.

Reference is now made to FIG. 2, which shows a muscular or gastric electrical activity positioning system 900 in operation while searching for the location of capsule 12 relative to a branch 934 of the vagus nerve, in accordance with a preferred embodiment of the present invention.

A Nerve Conduction Study (NCS) is a known non-invasive tool for measuring the speed of propagation or the rate at which an electrical impulse moves along a nerve. It is used for the diagnosis of disorders of the peripheral nerves and muscle. It is presently useful as a way of locating capsule 12 within stomach 16, and works by measuring and monitoring action potential that propagates along the nerve as a result of electrical stimulation. In a conventional NCS the nerve is stimulated, usually by surface electrodes which are placed on the skin over the nerve at various locations. The resulting electrical activity, recorded by recording electrodes, is known to have a high correlation with the stimulating sequence delivered by the surface electrode. Accordingly, by measuring the time difference between the activities at the surface electrodes and the recording electrodes, and knowing the distance therebetween, it is possible to calculate the speed of propagation. A significant deviation from a 'normal' speed is an indication of the existence of neural pathological conditions. It will be appreciated that if the stimulating electrode does not deliver the stimulation to the nerve, no neural activity will be recorded.

In operation of system 10, stimulating capsule 12 resides in stomach 16. When properly located, it will stimulate one of the branches of the vagus nerve 934. Excitation of the vagus nerve caused by operation of the capsule will propagate along the nerve, and can be identified by a surface detection and recording of the electrical activity of a proximal portion 938 of the vagus nerve. By way of example, recording surface electrodes 940 can be placed on the lower part of the patient's neck. The electrical signals detected by at least one pair of surface electrodes 940 are then transmitted to and analyzed by a recording and analyzing module 930. Module 930 may be a separate device which is connected to the remote control device 14, as shown, or it may be included within remote control device 14.

The stimulation pattern delivered by capsule 12 is determined by the analyzing recording module 930. The stimulation pattern may be either pre-defined or adaptive. With an adaptive scheme, capsule 12 can communicate the real time stimulation parameters to the analyzing device 930. Since the frequency of stimulation is known, analyzing/recording module 930 can employ a filtering algorithm, which may be implemented in software, hardware, or both, in order to identify the frequency of evoked potentials propagating along proximal portion 938 of the vagus nerve. If the stimulating frequency of the evoked potentials is identified as being the same as that of the stimulation frequency, it means that the vagus nerve is being successfully stimulated.

If the stimulating frequency is not identified as being the same as that of the stimulation frequency, however, this is taken to mean that the nerve is not stimulated, and that the location of capsule 12 and/or the stimulating parameters, such as amplitude, should be changed. It is appreciated that due to the physical size of capsule 12, it may advantageously positioned so as to be in proximity to other vagus nerve branches 936, so as to cause stimulation of the nerve.

In operation, prior to the patient or "user" ingesting capsule 12, the required region for the treatment by capsule 12 is typically externally marked on the patient's body. Positioning unit 900 is located outside the patient's body and in proximity to the required capsule location.

The above-described positioning system 900 operates as a feedback system. Following the securing of capsule 12 at the required location in proximity to vagus nerve branches 934 and 936, the operator and/or medical personnel select the operational parameters for the required medical treatment, and thereafter input the relevant capsule operational parameters and activate capsule 12.

Referring now also to FIGS. 1A and 1B, the patient then swallows capsule 12 and after a short period of time, usually in the region of approximately 10 minutes, capsule 12 enters the fundus region of the patient's stomach. The operator activates the position sensor 24 which commences a search for first magnetic element 40 located within capsule 12. Upon detecting the magnetic field generated by first magnetic element 40, the position sensor 24 forwards a "magnet-found" signal to control unit 22.

It will be appreciated that the present system may be used for treating different gastric disorders by adjustment of the operating parameters of the capsule electrodes.

For example, in order to generate a feeling of satiety so to control obesity, the values of the input parameters are typically in the following ranges:

Amplitude: 1-10 mA;
Frequency: 20-200 kHz, and
Waveform: symmetric or asymmetric Reference is now made to FIG. 3, which shows capsule 12 secured at different locations in the stomach 16 for treating different gastro disorders, in accordance with a preferred embodiment of the present invention.

Figure 3:
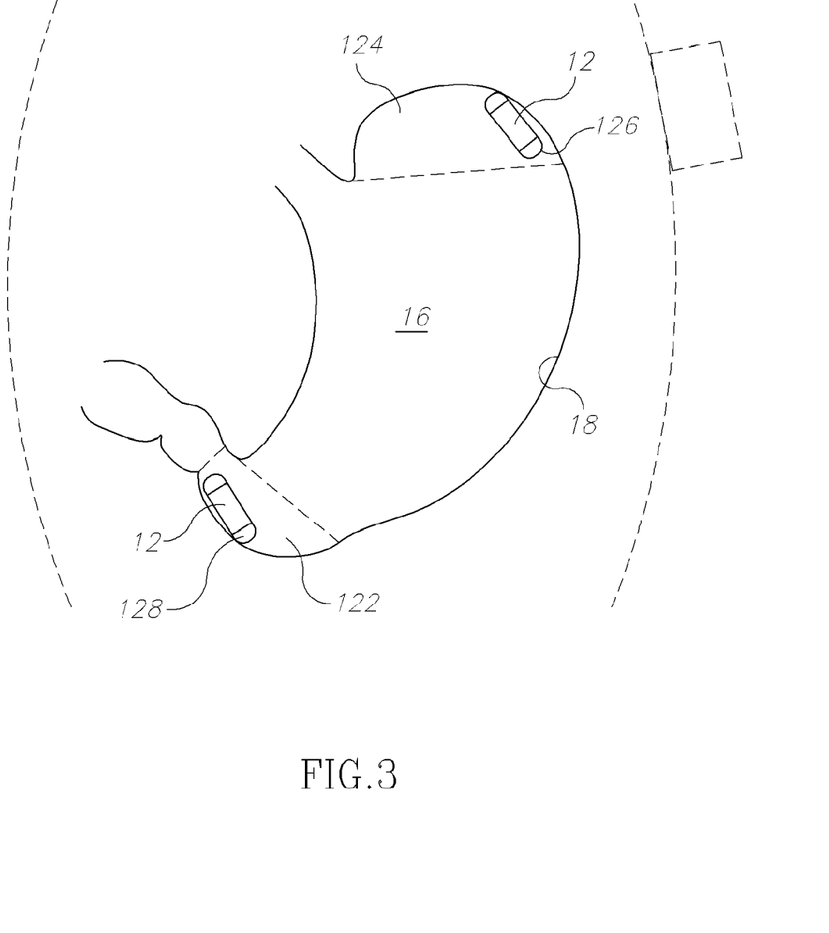
FIG. 3 shows the capsule secured at different locations in the GT for treating different gastro disorders, in accordance with an embodiment of the present invention.

At the various stomach locations, different branches of the vagus nerve may be stimulated in accordance with required medical treatments.

Thus, for treating stomach disorders of the stomach's fundus region 124, capsule 12 is positioned at location 126, while in order to treat gastro disorders of the stomach's pyloric region 122, capsule 12 is positioned at location 128.

By activating capsule 12 so as to stimulate one or more branches of the vagus nerve in proximity to various stomach locations, it is possible to control and monitor the function of the stomach, such as digestion and removal of food therefrom.

Referring now also to FIGS. 1A and 1B, on conclusion of the treatment protocol, stimulation system 10 is deactivated by inputting an appropriate "termination" instruction which is forwarded to capsule 12 via RF transceiver 32 to cease operation. Control unit 14 then forwards a "capsule-release" signal to position sensor 24 and an instruction for the operator or user to release the control device 14 from the patient's body, is displayed.

Figure 4A:
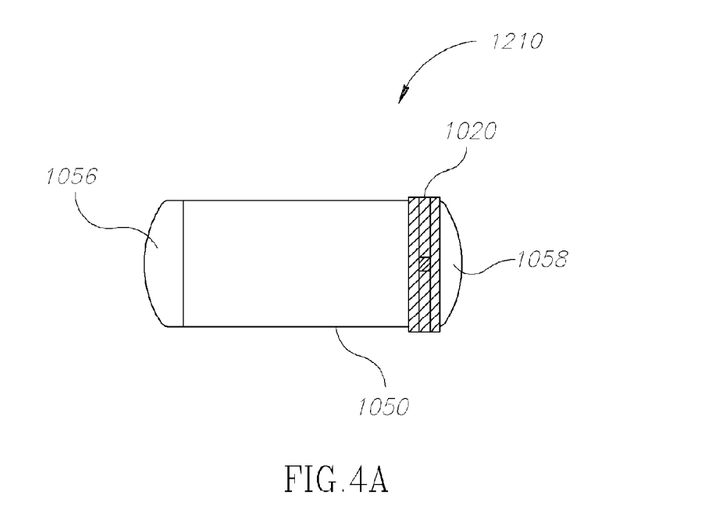
FIG. 4A shows a general view of a capsule, in accordance with another embodiment of the present invention.
Figure 4B:
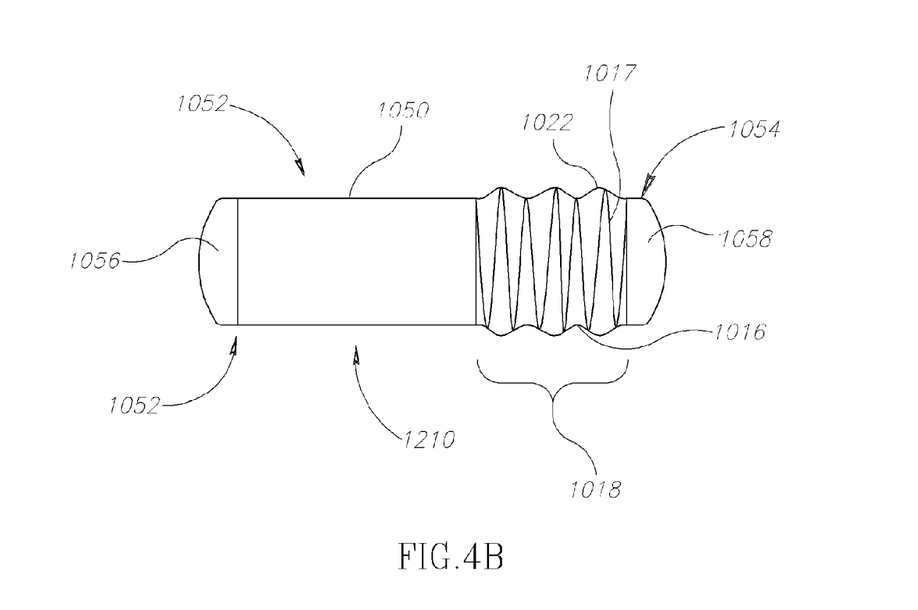
FIG. 4B shows the capsule of FIG. 4A in an extended state following ingression thereof into the GT, in accordance with another preferred embodiment of the present invention.

Reference is now made to FIGS. 4A and 4B, which show an extendible capsule 1210 which is generally similar to capsule 12, shown and described above in conjunction with FIGS. 1A-3, except as specifically described herein. Accordingly, components and portions of capsule 1210 are denoted in the drawings by reference numerals which are the same as their counterpart portions in FIGS. 1A-3, but with the addition of the prefix "10." Furthermore, these components and portions are not specifically described again herein except as may be necessary to understand the present embodiment of the invention.

An important feature of capsule 1210 is that it is adapted for egression from the pyloric region of the gastrointestinal tract after at least a predetermined dwell time. This is described at greater length below.

Extendible capsule 1210 has first and second portions, respectively referenced 1052 and 1054 (FIG. 4B) and a resilient element 1018 disposed therebetween. First portion 1052 includes main body portion 1050 of extendible capsule 1210 and first electrode 1056, and second portion 1054 consists of second electrode 1058. A gastric juice-responsive release unit 1020 coats resilient element 1018 in a non-extended state (FIG. 4A) and is operative to retain first and second capsule portions 1052 and 1054 portions in the non-extended arrangement in a first operative state of said capsule. Release unit 1020 is further operative, in response to contact with gastric juices for at least a predetermined period of time to permit the extendible capsule 1210 to move into a second operative state by release of resilient element 1018 so as to cause mutual extension thereby of first and second portions 1052 and 1054, thereby to extend the effective length of capsule 1210, as seen in FIG. 4B.

Resilient element 1018 includes an electrically-conductive expandable element 1017 (FIG. 4B) and a dielectric flexible membrane 1016. Expandable element 1017 may be a metallic spring, a leaf spring, a helical spring, a leaf spring having two arms, a pair of rigid arms movably joined to a spring at their meeting point, shape memory alloy member or other suitable compression member, extending from pulse generator 64 (FIG. 1B) to second electrode 1058 so as to conduct electrical signals thereto. A dielectric flexible membrane 1016 (FIG. 4B) is provided so as to connect between main body portion 1050 and second electrode 1058, and so as to surround and insulate expandable element 1017.

An advantage of capsule 1210 having a non-extended, compact state initially is that it is easier to swallow. Due to the dissolution of the gastric juice-responsive release unit 1020, the extendible unit 1018 expands so as to become fully deployed, and first and second electrodes 1056 and 1058 are moved apart. For example, if capsule 1210 when in a non-extended, first operative state has a length of 15 mm, after the gastric juice-responsive release unit 1020 is dissolved, the length of capsule 1210 may extend to approximately 30 mm. Extension of capsule 1210 renders it more likely that the electrodes will engage at least one branch of the vagus nerve or other selected region of the GT (FIG. 3).

Gastric juice-responsive release unit 1020 is formed of a material that is dissolvable under different endo-luminal conditions, such as low pH, temperature and enzymatic degradation. Thus, release unit 1020 may be formed of a material known to dissolve in a predetermined portion of the stomach. Suitable materials include a biodegradable polymer, such as Poly(lactic-co-glycolic acid) (PLGA); any of a variety of sugars, for example, a caramel substance; or an enteric material.

Figure 5A:
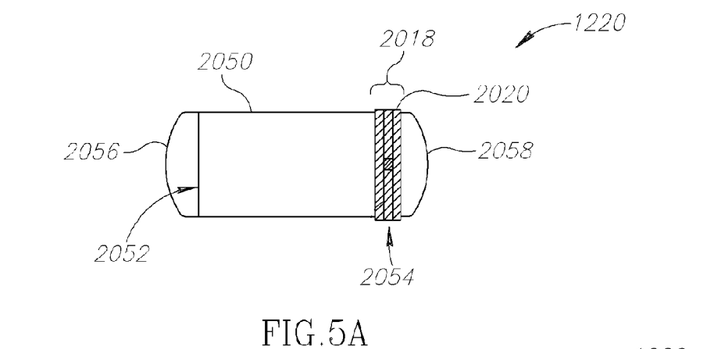
FIG. 5A shows a general view of a capsule, in accordance with yet another embodiment of the present invention, in a first operative state.
Figure 5B:
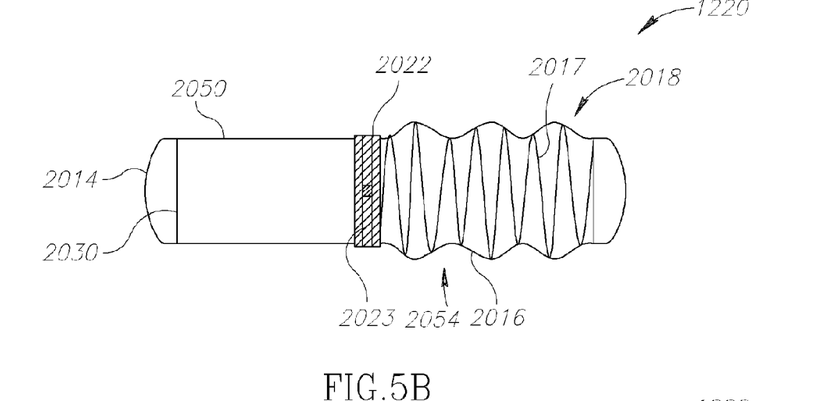
FIG. 5B shows the capsule of FIG. 5A in an extended, second operative state following ingression of the capsule into the GT.
Figure 5C:
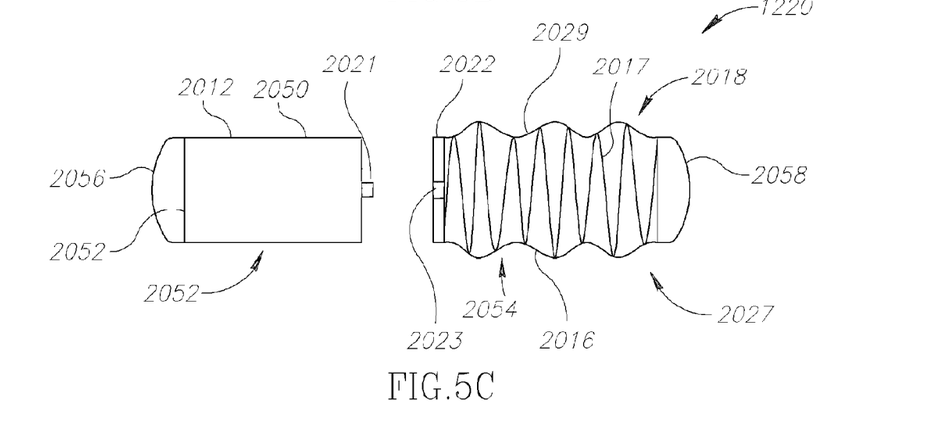
FIG. 5C shows the capsule of FIGS. 5A and 5B in a severed, third operative state.

Reference is now made to FIGS. 5A-5C, which show an extendible capsule 1220, constructed and operative in accordance with another embodiment. Capsule 1220 is generally similar to capsule 1210, shown and described above in conjunction with FIGS. 4A-4B, except as specifically described herein. Accordingly, components and portions of capsule 1220 are denoted in the drawings by reference numerals which are the same as their counterpart portions in FIGS. 4A-4B, but with the addition of the prefix "10" by the prefix "20". Furthermore, these components and portions are not specifically described again herein except as may be necessary to understand the present embodiment of the invention.

Extendible capsule 1220 has first and second portions, respectively referenced 2052 and 2054 (FIG. 5C) and resilient element 2018 disposed therebetween. First portion 2052 includes main body portion 2050 of extendible capsule 1220 and first electrode 2056 and second portion 2054 consists of electrode 2058. Gastric juice-responsive release unit 2020 coats resilient element 2018 when in a non-extended state (FIG. 5A) and is operative to retain first and second capsule portions 2052 and 2054 portions in the non-extended arrangement in a first operative state of said capsule. Release unit 1020 is further operative, in response to contact with gastric juices for at least a predetermined period of time to permit the extendible capsule 1220 to move into a second operative state by release of resilient element 2018 so as to cause mutual extension thereby of first and second portions 2052 and 2054, thereby to extend the effective length of capsule 1220, as seen in FIG. 5B.

Gastric juice-responsive release unit 2020 differs from unit 1020 of capsule 1210 described in conjunction with FIGS. 4A and 4B, since it consists of first and second selectably releasable, gastric juice-responsive, locking elements, respectively referenced 2020 (FIG. 5A) and 2022 (FIG. 5B). First locking element 2020 is used for resisting an urging force of resilient element 2018, thereby locking together first and second capsule portions 2052 and 2054 in a non-extended arrangement when capsule 1220 is in first operative state (FIG. 5A). Second locking element 2022 is operative to maintain a mechanical connection between first and second capsule portions 2052 and 2054 when capsule 1220 is in extended arrangement in second operative state, after which, in a third operative state, second locking element 2022 is operative to disconnect first and second capsule portions 2052 and 2054 from each other (FIG. 5C), as described below in more detail.

Resilient element 2018 includes an electrically-conductive expandable element 2017 (FIG. 5B) and a dielectric flexible membrane 2016. Expandable element 2017 may be a metallic spring, a leaf spring, a helical spring, a leaf spring having two arms, a pair of rigid arms movably joined to a spring at their meeting point, shape memory alloy member or other suitable compression member, extending from pulse generator 64 (FIG. 1B) to second electrode 2058 so as to conduct electrical signals thereto. A dielectric flexible membrane 2016 (FIG. 5B) is provided so as to connect between main body portion 2050 and second electrode 2058, and so as to surround and insulate expandable element 2017.

Resilient element 2018 is similar to resilient element 1018 (FIGS. 4A and 4B), except that it is formed not only to extend after dissolution of the gastric-juice responsive release unit 2020, but also so as to subsequently become completely detached from the main body portion 2050, thereby to ease the excretion of the extended capsule 1220 from the stomach, after capsule portions 2052 and 2054 detach from each other, as seen in FIG. 5C.

As seen in FIG. 5C. distal end of first portion 2052 of main body portion 2050 terminates in a connector having a pin 2021 which is conductively connected to the pulse generator 64 (FIG. 1B) of capsule 1220.

Expandable element 2017 (FIGS. 5B and 5C) may be a metallic spring or other suitable compression member described above in relation to expandable element 1017 (FIG. 4B). It extends typically from a socket 2023 formed in a proximal end member 2029 of extendible unit 2018 in second portion 2054 of capsule 1220, to the second electrode 2058. The connection between pin 2021 and socket 2023 is operative to conduct electrical signals from pulse generator 64 to second electrode 2058. Dielectric flexible membrane 2016 (FIGS. 5B and 5C) is provided so as to mechanically connect proximal end member 2029 of extendible unit 2018 to second electrode 2058, and so as to surround and insulate expandable element 2017.

In the present embodiment, the two gastric juice-responsive locking elements 2020 and 2022 have predetermined different rates of dissolution. First locking element 2020 is formed of a first gastric-juice soluble substance which is soluble at a first predetermined rate so as to permit extension of said capsule 1220 after a first dwell time in the gastrointestinal tract of a patient. Second locking element 2022 is formed of a second gastric-juice soluble substance which is soluble at a second predetermined rate so as to disconnect said first 2052 and second 2054 capsule 1220 portions from each other permit after a second dwell time in the gastrointestinal tract of a patient, the second dwell time being longer than the first dwell time.

An advantage of capsule 1220 having a non-extended, compact state initially, is that it is easier to swallow. Due to the dissolution of gastric juice-responsive release unit 2020 once in the stomach, the extendible unit 2018 expands so as to become fully deployed, and the longitudinal dimension of capsule 1220 between the first electrode 2056 and the second electrode 2058 is increased, as shown in FIGS. 4A and 4B, and as described in conjunction therewith with regard to capsule 1210.

Gastric juice-responsive locking elements 2020 and 2022 are formed of materials substantially as described above in relation to gastric juice-responsive release unit 1020 of capsule 1210.

Reference is now made to FIGS. 6A-6E, which show a capsule 1230, constructed and operative in accordance with another embodiment of the present invention. Capsule 1230 is generally similar to capsule 12, shown and described above in conjunction with FIGS. 1A-3, except as specifically described herein.

Accordingly, components and portions of capsule 1230 are denoted in the drawings by reference numerals which are the same as their counterpart portions in FIGS. 1A-3, but with the addition of the prefix "30." Furthermore, these components and portions are not specifically described again herein except as may be necessary to understand the present embodiment of the invention.

Figure 6A:
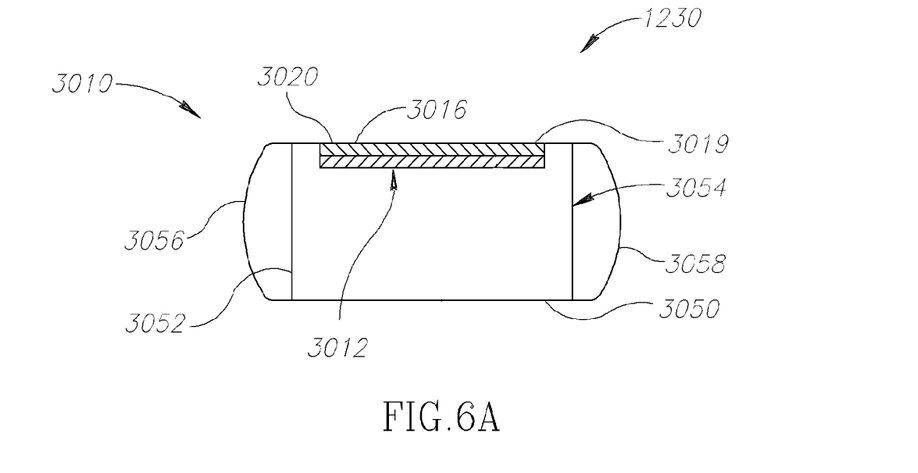
FIGS. 6A-6C show a capsule adapted to float on gastric juices, in accordance with a further embodiment of the present invention, in a first operative state.
Figure 6B:
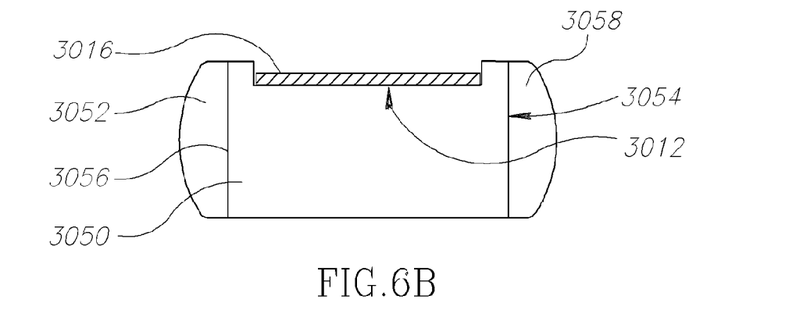

Capsule 1230 includes at least one gastric juice-responsive expandable element, which is shown in FIGS. 6A-6E in different states and denoted by reference numeral 3016. In the present example three are shown although one or more may be used as required. These elements are adapted for storage within a storage compartment 3012 formed within main body portion 3050 of capsule 1230 (FIG. 6A). A gastric juice-responsive cover 3020 closes storage compartment 3012 and prevents expandable elements 3016 from exposure to gastric juices. Cover 3020 is formed of a first gastric-juice soluble substance which is soluble at a first predetermined rate so as to permit exposure of expandable elements 3016 to gastric juices after a first dwell time in the gastrointestinal tract of a patient.

Cover 3020 may be made of a material similar to that of gastric juice-responsive locking element 2020 (FIG. 5A) as described above. When gastric-juice responsive cover 3020 dissolves it opens storage compartment 3012 so as to expose expandable elements 3016 to gastric juices. Due to this exposure, elements 3016 expand so as to be forced out of storage compartment 3012 and so as to increase the overall size of capsule 1230, thereby preventing capsule 1230 from egression from the pyloric region of the stomach.

Figure 6C:
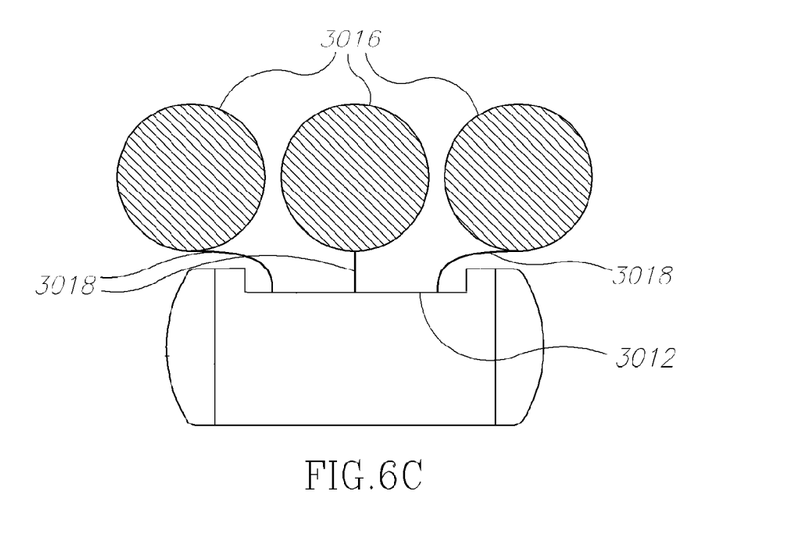

Each expandable element 3016 is connected to main body portion 3050 of capsule 1230 by means of a gastric-juice responsive releasable connector element 3018 (FIG. 6C). Expandable elements 3016 are typically formed of a super-absorbent polymer (SAP), and connector elements 3018 are made from soluble from absorbable surgical sutures.

Cover 3020 is formed of a first gastric-juice soluble substance which is soluble at a first predetermined rate so as to permit exposure of expandable elements 3016 to gastric juices after a first dwell time in the gastrointestinal tract of a patient. Connector elements 3018 is formed of a second gastric-juice soluble substance which is soluble at a second predetermined rate so as to dissolve connector elements 3018 after a second dwell time in the gastrointestinal tract of a patient, wherein the second dwell time is longer than the first dwell time.

Figure 6D:
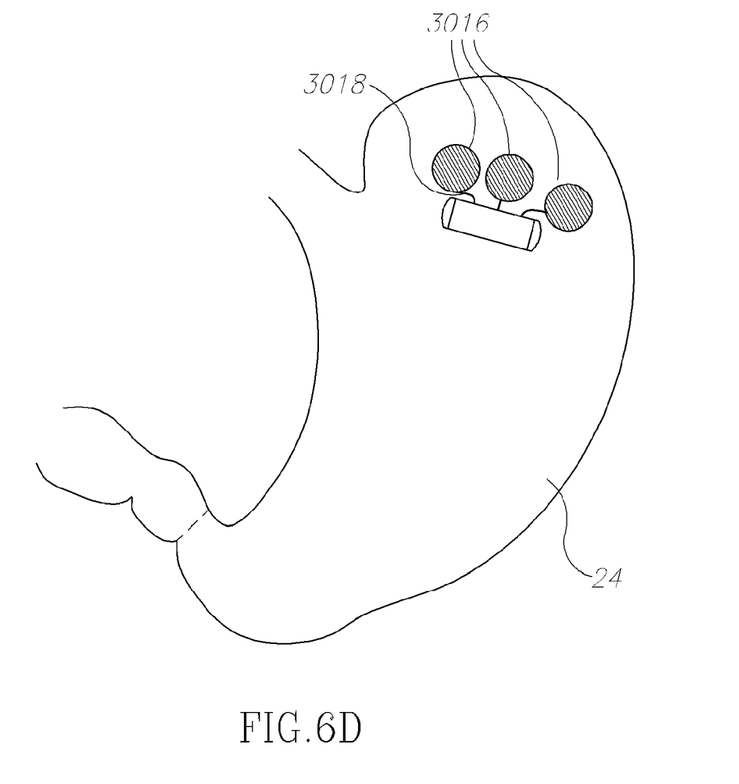
FIG. 6D shows the capsule of FIGS. 6A-6C in a deployed, second operative state, floating within the pyloric region of the patient's stomach.
Figure 6E:
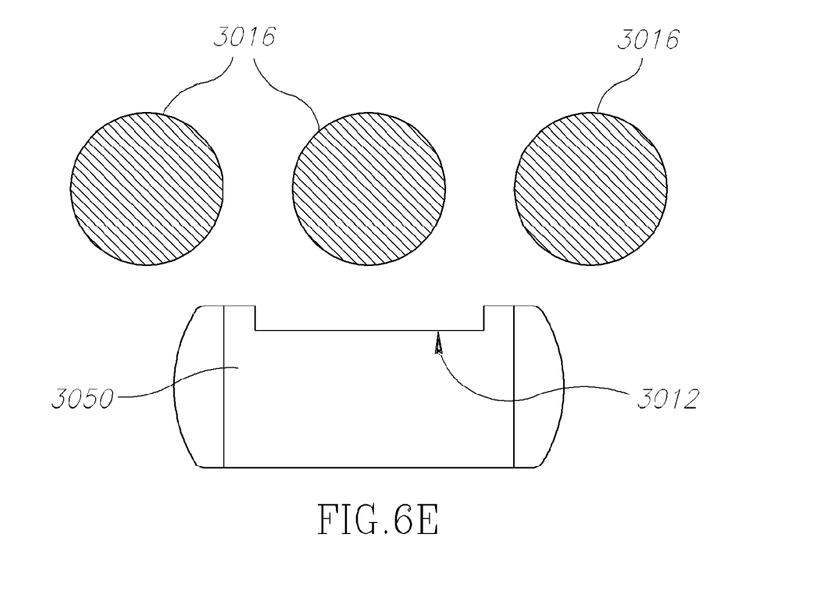
FIG. 6E shows the capsule of FIGS. 6A-6D in a disconnected, third operative state.

Referring now briefly to FIG. 6D, capsule 1230 with SAP elements 3016 is seen to be floating within the patient's stomach 24. As seen in FIG. 6E, after a predetermined stay in the stomach, connector elements 3018 dissolve, thereby releasing the expandable elements 3016 from capsule 1230 and so enabling both the capsule and the expandable elements 3016 to be excreted. Typically, connector elements 3018 are formed so as to dissolve after a stay or dwell time in the stomach normally in the range 48-72 hours.

It will be appreciated floating capsule 1230 as described above obviates the need for a user to wear a control device such as control device 14 (FIG. 1A) except during the positioning of capsule 1230, thereby rendering its use more comfortable.

Figure 7A:
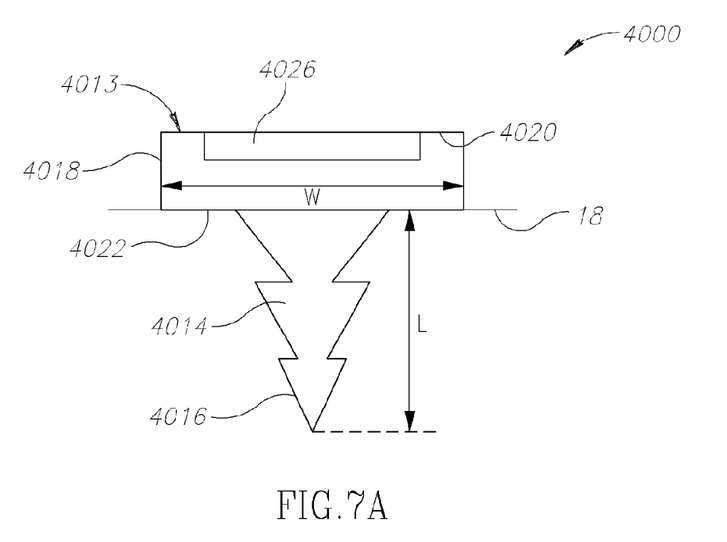
FIGS. 7A and 7B show an implantable gastrointestinal tract capsule-securing device for securing a capsule adapted for ingression into the GT and having an integral electrode, in accordance with an embodiment of the present invention.
Figure 7B:
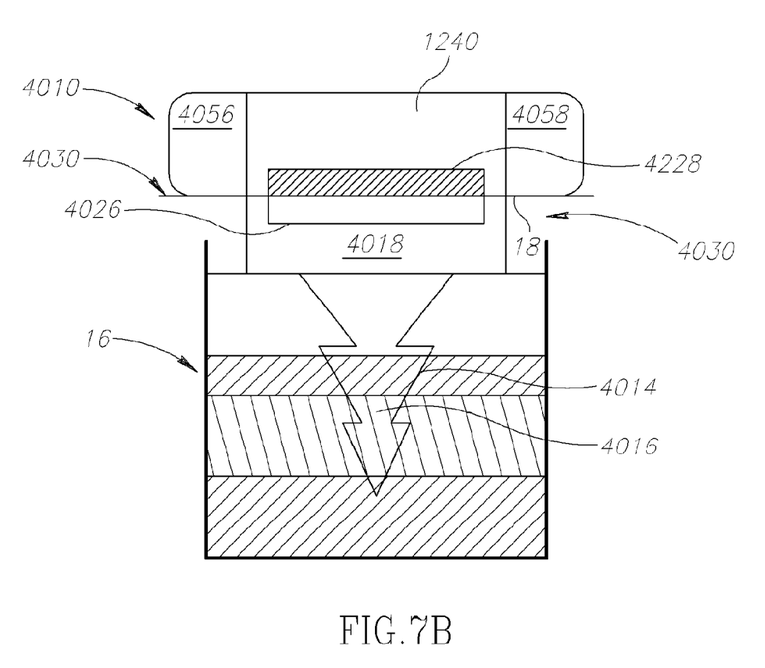

Reference is now made to FIGS. 7A and 7B, which show an implantable gastrointestinal tract capsule-securing device 4000 for securing a capsule 1240 adapted for ingression into the GT 16, in accordance with yet a further embodiment of the present invention. The capsule-securing device 4000 includes, inter alia, a location pin 4013 comprising a pin shaft 4014 and a pin head 4018 having an upper surface 4020 and a lower surface 4022. Pin shaft 4014 is attached to the lower surface 4022 of the pin head 4018 and includes preferably a serrated outer edge 4016 for mechanically securing the device 4000 within the GT 16. The device 4000 is implanted into the wall 18 of the GT 16 at a required location, by a known medical method, such as gastrointestinal endoscopy and the device 4000 is secured in the GT 16 by inserting the serrated edge 4016 into the wall 18 of the GT 16 (FIG. 7A). The serrated edge 4016 grips the wall of the GT 16 at the required location in the GT 16, and the lower surface 4022 of the pin head 4018 abuts against the outer surface of the wall 18 of the GT 16.

In the present embodiment the system includes a capsule 1240 adapted for ingression into the gastrointestinal tract of a patient, and a magnetic coupling system for securing capsule 1240 within the gastrointestinal tract 16 of the patient, wherein the coupling system has a first magnetic element 4228 associated with capsule 1240 (FIG. 7B) and a second magnetic element configured for placement externally of the body of the patient (not shown in FIGS. 7A and 7B). Capsule system also includes at least one capsule-securing device 4000 implantable in the wall 18 of the gastrointestinal tract 16 at a selected location and a third magnetic element 4026 associated with location pin 4013 (FIG. 7A).

In FIG. 7B, the pin head 4018 is seen to include a magnetic element 4026. In combination with the magnetic element 4228 located within capsule 1240, the pin head magnetic element 4026 forms a magnetic coupling system 4030 for magnetically securing the capsule 4012 to the capsule-securing device 4000. The capsule 1240 is attached to the pin head 4018 by the magnetic attraction between the magnetic element 4228 and the magnetic element 4026.

The length L (FIG. 7A) of the pin shaft 4014 is predetermined in accordance with the required location the pin shaft 4014 in the GT 16 (FIG. 7A). Preferably, the pin shaft 4014 should have a longitudinal length which is approximately 50-80% of the thickness of the wall 18 at the required location in the GT 16. For example, if the pin shaft 4014 is to be inserted into the stomach of the patient, it should have a length, L, of approximately 2.5-4 mm, assuming that the average stomach thickness of the patient is approximately 5 mm.

Preferably, the width W of the pin head 4018 is approximately 3-5 times the length L of the pin shaft 4014 and is approximately 7.5-12 mm.

Figure 8:
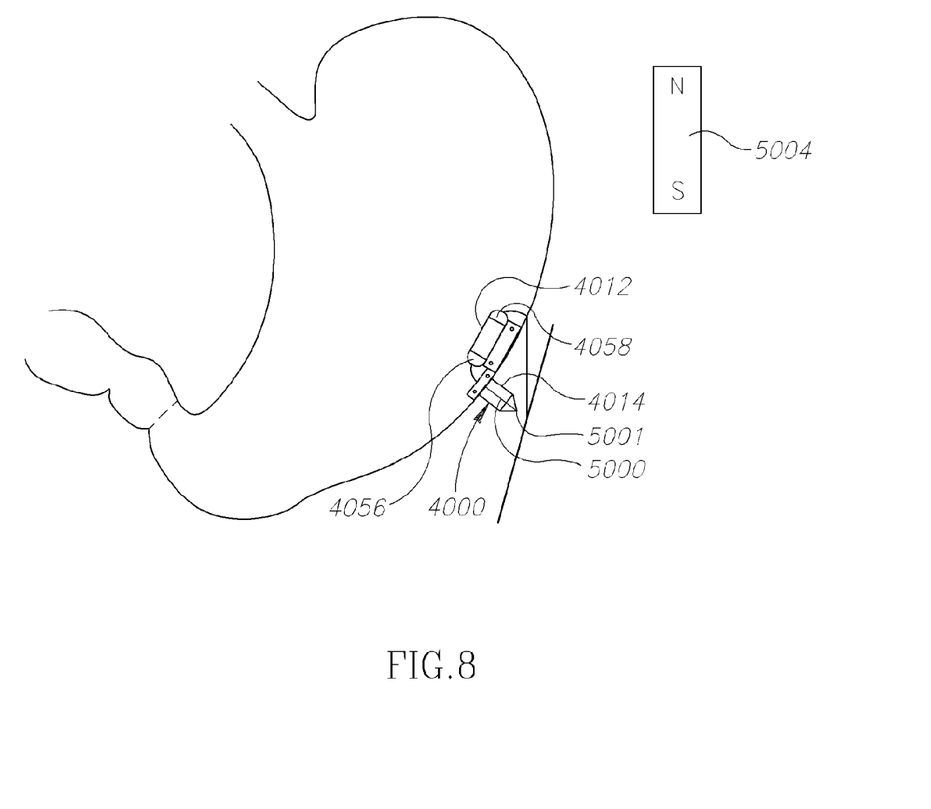
FIG. 8 shows use of the capsule of the invention in conjunction with a single device of FIGS. 7A and 7B.
Figure 9:
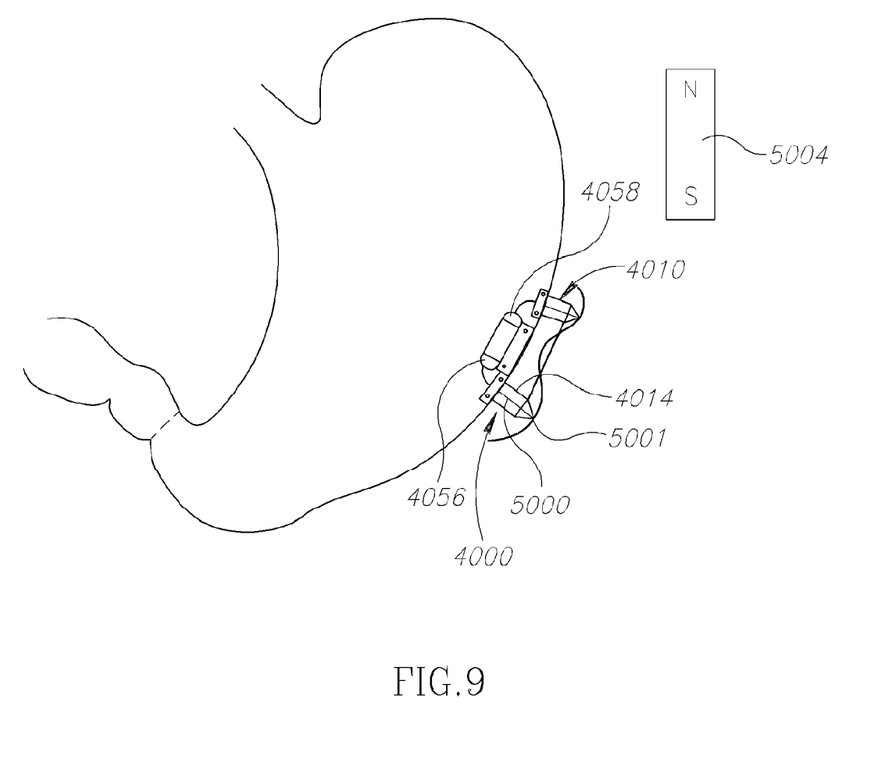
FIG. 9 shows use of the capsule of the invention in conjunction with a pair of the devices of FIGS. 7A and 7B.

In accordance with a further embodiment of the invention, and referring now to FIGS. 8 and 9, device 4000 may have an electrode 5000 (FIGS. 8 and 9) formed integrally therewith, such that it can be advantageously positioned so as to be in electrically conductive connection with one of the electrodes 4056 or 4058. As the pin shaft 4014 extends through the stomach wall and into closer proximity with the vagus nerve or other chosen area, the ability to provide the electrical signals from the electrodes of capsule 1240 to an electrode terminating at the tip 5001 of the pin shaft 4014, increases the ease of positioning and effectiveness of the treatment. In this embodiment, device 4000 is seen to secure the capsule to the stomach wall magnetically so that the capsule is positioned on the pin head, but next to it, by appropriate positioning of magnetic axis.

FIG. 8 illustrates the use of a single device 4000 to secure capsule 1240, while FIG. 9 illustrates the use of a pair of devices, 4000 and 4010, both of which convey electrical signals into proximity with the vagus nerve or other chosen area.

Referring now particularly to FIG. 8, use of the presently described system is thus as follows:

The pin device 4000 is implanted into the stomach wall at a desired location.

Capsule 1240 is ingested into the stomach.

A powerful, guiding magnet 5004 is used by an operator to guide the capsule 4012 to the location of the implanted pin device 4000, so as to expose the capsule to the magnetic field of the pin device's magnet.

The guiding magnet is removed, and the capsule remains magnetically secured to pin device 4000, after which the capsule is operated and treatment can commence.

After termination of treatment, the guiding magnet 5004 is used to magnetically drag capsule 1240 away from pin device 4000, after which the capsule will be able to exit the body.

It will be appreciated that this approach obviates the need for a patient to wear a magnet during the treatment.

It will be appreciated by persons skilled in the art that the scope of the present invention is not limited by what has been particularly shown and described hereinabove with reference to the drawings. Rather, the scope of the present invention is limited solely by the claims which follow.

We claim:
1. A gastrointestinal electro stimulation system including:
(I) a remote controlled capsule adapted for ingression into the gastrointestinal tract of a patient,
(II) a remote control device for controlling and sharing information with said capsule, and
(III) a magnetic coupling system for securing said capsule within the gastrointestinal tract of the patient, wherein said capsule has a main body portion and a plurality of electrodes arranged in electrical isolation from each other, said capsule containing:
 (a) a first RF transceiver operative to receive capsule operating instructions from and to transmit information to said remote control device;
 (b) a capsule control unit electrically coupled to said first RF transceiver and operative to process said received operating instructions;
 (c) a pulse generator electrically coupled to said capsule control unit and to said electrodes and configured to activate said electrodes so as to emit electrical stimuli pulses in accordance with said operating instructions; and
 (d) a power supply for supplying electrical power to said first RF transceiver, to said control unit and to said pulse generator,
wherein said remote control device comprises:
 (e) a system control unit operative to generate said operating instructions;
 (f) a second RF transceiver coupled to said system control unit and configured to transmit said operating instructions and to receive information from said first RF transceiver,
and wherein said magnetic coupling system comprises:
 (g) a first magnetic element associated with said capsule and a second magnetic element configured for placement externally of the body of the patient,
wherein selectable operation of said pulse generator is operative to expose to electrical stimuli a portion of the gastrointestinal tract where said capsule is secured, and
wherein said capsule is further adapted for egression from the pyloric region of the gastrointestinal tract after at least a predetermined dwell time therein, and wherein said main body portion of said capsule includes:
 at least one gastric juice-responsive expandable element adapted for storage within a storage compartment formed within said main body portion of said capsule; and
 a gastric-juice responsive cover for said storage compartment which when closed, prevents said at least one expandable element from exposure to gastric juices and, when open, facilitates exposure of said at least one expandable element to gastric juices such that said element expands so as to be forced out of said storage compartment and so as to increase the overall size of said capsule system thereby preventing said system from egression from the pyloric region of the stomach,
wherein said at least one expandable element is connected to said main body portion of said capsule by means of a gastric-juice responsive releasable connector element.

2. A gastrointestinal electro stimulation system according to claim 1, wherein said gastric-juice responsive cover is formed of a first gastric-juice soluble substance which is soluble at a first predetermined rate so as to permit exposure of said expandable element to gastric juices after a first dwell time in the gastrointestinal tract of a patient, and
 said gastric-juice responsive releasable connector element is formed of a second gastric-juice soluble substance which is soluble at a second predetermined rate so as to dissolve said connector element after a second dwell time in the gastrointestinal tract of a patient, said second dwell time being longer than said first dwell time,
 wherein dissolution of said connector element causes detachment of said at least one expandable element from said main body portion of said capsule, thereby permitting egression of said capsule from the gastrointestinal tract.

3. A gastrointestinal electro stimulation system according to claim 2, wherein each said expandable element is adapted to expand to a size which is sufficiently small to permit egression thereof from the gastrointestinal tract.

4. An extendible capsule adapted for ingression into the gastrointestinal tract of a patient, which includes:
 first and second capsule portions;
 a resilient element disposed between said first and second capsule portions for normally urging them apart into an extended arrangement; and
 a gastric juice-responsive release unit operative to retain said first and second capsule portions in a non-extended arrangement in a first operative state of said capsule, and further operative, in response to contact with gastric juices for at least a predetermined period of time to permit said capsule to move into a second operative state by mutual extension of said first and second capsule portions thereby to extend the effective length of said capsule.

5. An extendible capsule according to claim 4, wherein said gastric juice-responsive release unit includes:
 a first gastric juice-responsive locking element for resisting an urging force of said resilient element, thereby locking together said first and second capsule portions in said non-extended arrangement when said capsule is in said first operative state; and
 a second gastric juice-responsive, selectably releasable locking element operative to maintain a mechanical connection between said first and second capsule portions when said capsule is in said extended arrangement in said second operative state, wherein said first and second locking elements are adapted to selectably disconnect said first and second capsule portions from each other so as to move said capsule into a third operative state,
 wherein, when said capsule is in said first operative state, said first locking element is deactivated, such that said resilient element is operative to force said first and second capsule portions and thus said capsule into said extended arrangement of said second operative state,
 and wherein, said second locking element is subsequently deactivated so as to disconnect said first and second capsule portions from each other such that said capsule splits into two portions and moves into said third operative state.

6. An extendible capsule according to claim 5, wherein
 said first gastric juice-responsive locking element is formed of a first gastric-juice soluble substance which is soluble at a first predetermined rate so as to permit extension of said capsule after a first dwell time in the gastrointestinal tract of a patient, and
 said second gastric juice-responsive locking element is formed of a second gastric-juice soluble substance which is soluble at a second predetermined rate so as to disconnect said first and second capsule portions from each other after a second dwell time in the gastrointestinal tract of a patient, said second dwell time being longer than said first dwell time.

7. An extendible capsule according to claim 4, wherein said gastric juice-responsive release unit is formed of a solid substance which is soluble in gastric juices.

8. An extendible capsule according to claim 4, wherein said first capsule portion includes a main body portion formed of a dielectric material, and a first electrode, and said second capsule portion includes a second electrode, wherein said first capsule portion contains:
- (i) an RF transceiver operative to receive capsule operating instructions from a remote control unit and to transmit information thereto;
- (ii) a capsule control unit electrically coupled to said RF transceiver and configured to process received operating instructions;
- (iii) a pulse generator electrically coupled to said capsule control unit and to said first and second electrodes and configured to activate said first and second electrodes so as to emit electrical stimuli pulses in accordance with said processed operating instructions, and
- (iv) a power supply for supplying electrical power to said RF transceiver, to said control unit and to said pulse generator, and wherein upon extension of said capsule, said first and second electrodes are moved laterally apart so to increase the distance between them, and thus to expose a greater portion of the GI tract to said electrical stimuli pulses.

9. For use with a gastrointestinal capsule system which includes a capsule adapted for ingression into the gastrointestinal tract of a patient, and a magnetic coupling system for securing the capsule within the gastrointestinal tract of the patient, wherein the coupling system has a first magnetic element associated with the capsule and a second magnetic element configured for placement externally of the body of the patient, at least one capsule-securing device implantable in the wall of the gastrointestinal tract at a selected location, said capsule-securing device including:
a location pin; and
a third magnetic element associated with said location pin,
wherein, when the capsule is located within the gastrointestinal tract of the patient, movement of the second magnetic element, externally of the patient's body, to a position corresponding to that of said capsule-securing device, causes a corresponding movement of the first magnetic element and a consequent magnetic coupling of the first and said third magnetic elements, thereby to position said capsule at said selected location in the gastrointestinal tract.

10. A capsule securing device according to claim 9, wherein said location pin includes:
- a pin head having an upper surface to which said third magnetic element is secured and a lower surface for engaging the wall of the gastrointestinal tract when implanted therein; and
- a pin shaft extending from said lower surface and having a serrated outer edge for mechanically securing said device to the inner wall of the gastrointestinal tract.

11. The gastrointestinal system according to claim 9, wherein the system is a gastrointestinal system and the capsule is used for gastrointestinal electro stimulation, and wherein said capsule-securing device is formed of an electro-conductive material.

* * * * *